US00PP28019P3

(12) United States Plant Patent
Byrne et al.

(10) Patent No.: US PP28,019 P3
(45) Date of Patent: May 16, 2017

(54) PEACH TREE NAMED 'GOLDEN ZEST'

(50) Latin Name: *Prunus persica*
Varietal Denomination: Golden Zest

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 110 days.

(21) Appl. No.: 14/544,520

(22) Filed: Jan. 13, 2015

(65) Prior Publication Data

US 2016/0205840 P1 Jul. 14, 2016

(51) Int. Cl.
*A01H 5/08* (2006.01)

(52) U.S. Cl.
USPC ..... Plt./197

(58) Field of Classification Search
USPC ..... Plt./197
See application file for complete search history.

(56) References Cited

U.S. PATENT DOCUMENTS

PP7,953 P 8/1992 Bradford et al.

OTHER PUBLICATIONS

"Royal and Golden Zest Peaches," Texas A&M AgriLIFE, Feb. 8, 2013.*

The Brooks and Olmo Register of Fruit and Nut Varieties, 3rd Ed., American Society of Horticultural Science Press, Alexandria, VA, 1997.

Brooks, R. M. 1958. Double Delight, Earligold, and Jun. Gold peaches. Fruit Var. J. 3:22.

Okie, W. R., D. W. Ramming, and R. Scorza. 1985. Peach, nectarine, and other stone fruit breeding by the USDA in the last two decades. HortScience 20: 633-641.

Raseira, M. C. B., B. H. Nakasu, A. M. Santos, J. F Fortes, O. M. Martins, A. Raseira, and J. Bernardi. 1992. The CNPFT/EMBRAPA fruit breeding program in Brazil. HortScience 27: 1154-1157.

* cited by examiner

*Primary Examiner* — Anne Grunberg
(74) *Attorney, Agent, or Firm* — Ramey & Schwaller, LLP

(57) ABSTRACT

Disclosed is a new variety of *Prunus persica* named 'GOLDEN ZEST'. This new variety, which requires approximately 600 chilling units of dormancy, is considered to be a peach tree of mid-season maturity, which produces yellow-fleshed fruit with non-melting firm flesh, attractive golden yellow skin coloration, and suitable for both local and long-distance shipping.

5 Drawing Sheets

BACKGROUND OF THE INVENTION

Field of the Invention

This invention relates to peach trees and, more specifically, to peach trees referred to as a variety of *Prunus persica* named 'Golden Zest. 'Golden Zest, which requires approximately 600 chilling units of dormancy, produces an exceptionally high quality, firm, non-melting, yellow-fleshed, clingstone peach that matures in mid-season.

SUMMARY OF THE INVENTION

The 'Golden Zest' peach is characterized as to novelty and is otherwise noteworthy by producing fruit that ripens in the mid-season; is considered high quality; and which has firm, non-melting yellow flesh and has an attractive golden yellow skin coloration. In this regard, the present variety of peach tree bears fruit that are ripe for commercial harvesting and shipment in mid to late June, when the fruit is grown in medium chill zone of Texas. 'Golden Zest' ripens 15-21 days after 'June Gold' peach, a non-patented variety (Brooks, R. M. 1958. Fruit Var. J. 3:22), and its female parent, 'Crimson Lady' (Bradford and Bradford, 1992; U.S. Plant Pat. No. 7,953). 'Golden Zest' requires about 600 chilling units to break dormancy which is less than its female parent 'Crimson Lady' and more than its pollen (male) parent 'Agata' (not patented). Additionally, the new variety exhibits the potential to be commercialized in medium chill regions which receive about 600 chilling units per year.

Origin of the Variety

The present peach tree was the result of an ongoing Stone Fruit Breeding Program of Texas A & M University, College Station, Brazos County, Tex. To this end, controlled crosses are made each year in order to produce seedling populations from which improved progenies are evaluated and selected. The seedling TX4E220C originated at the Texas A & M University Horticultural Farm in College Station, Tex. in 2002, and was chosen from a population of seedlings. 'Golden Zest' is from a cross between the California peach cultivar 'Crimson Lady' (Bradford and Bradford, 1992; U.S. Plant Pat. No. 7,953) and the Brazilian non-melting cultivar 'Agata' (not patented). 'Crimson Lady' is a high chill, early ripening, nonmelting, yellow-flesh, clingstone peach released by Bradford in 1992 which resulted from a cross between the 'Red Diamond' nectarine (U.S. Plant Pat. No. 3,165) and the 'Springcrest' peach (not patented; Okie et al., 1985). 'Agata' (Conserva 458, not patented) a non-melting, processing peach, was released in 1985 by the EMBRAPA Fruit Breeding Program in Pelotas, Rio Grande do Sul, Brazil (Raseira et al., 1992). It is a selection from an open pollinated seed from the unreleased selection 682011041 (not patented) acquired from Dr. Hough at Rutgers University in 1972. This selection was derived from a cross between an unreleased non-melting selection from New Jersey (NJC95, not patented) and a non-melting, freestone from South Africa (SN45/3).

Resulting seed from this cross were planted in 1999 at the Texas A & M University Horticultural Farm in College Station, Tex. 'Golden Zest' was marked as TX4E220C for subsequent observation and noted as having exceptional characteristics. Two-year and older trees of the variety were subsequently evaluated during the 2005 through 2013 fruit growing seasons in both California (Fowler) and Texas (Terrell, Fairfield and College Station).

Asexual Reproduction of the Variety

'Golden Zest' was bud grafted onto virus-free Nemaguard (Brooks and Olmo 1997) peach rootstock in June 1998 at the nursery site in Oakdale, Calif. The variety was subsequently planted at the experimental orchard in the central portion of the San Joaquin Valley, near Fowler, Fresno County, Calif. and in two sites in Texas (College Station, Fairfield, and Terrell). Fruit from the resulting propagation has been evaluated during the period from 2000 to 2008 fruit seasons. This evaluation clearly demonstrated that the repropagated trees were true to the characteristics of the original seedling in all observable aspects.

BRIEF DESCRIPTION OF THE DRAWINGS

This new variety of peach tree is illustrated by the accompanying photographic drawings and depicts the plant by the best possible color representation using color photography, wherein.

BOTANICAL DESCRIPTION OF THE VARIETY

Figure 1:
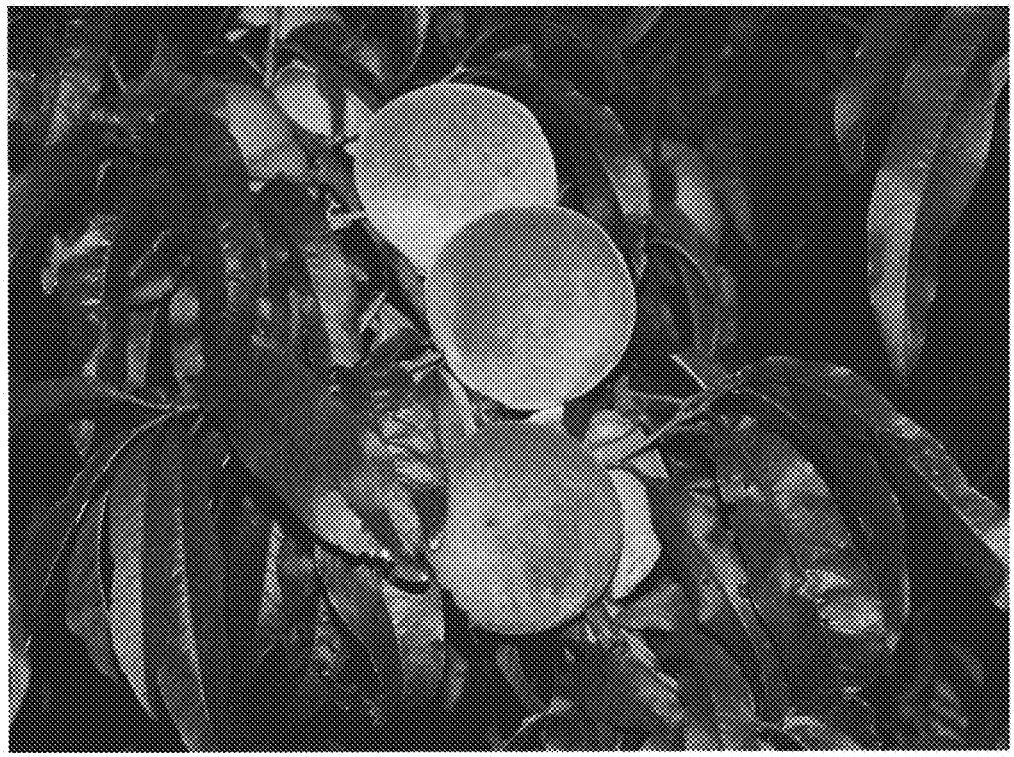
FIG. 1. A color photograph of a characteristic twig bearing typical leaves and several mature fruit showing their external coloration sufficiently matured for harvesting and shipment of 'Golden Zest'.
Figure 2:
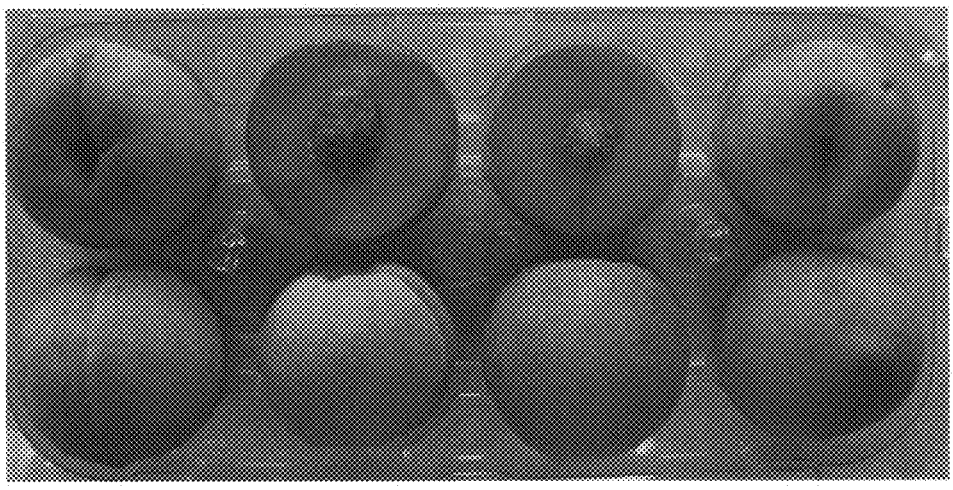
FIG. 2. Color picture showing the flesh and skin color and fruit shape of 'Golden Zest' produced in the medium chill zone of Texas (Fairfield).
Figure 3:
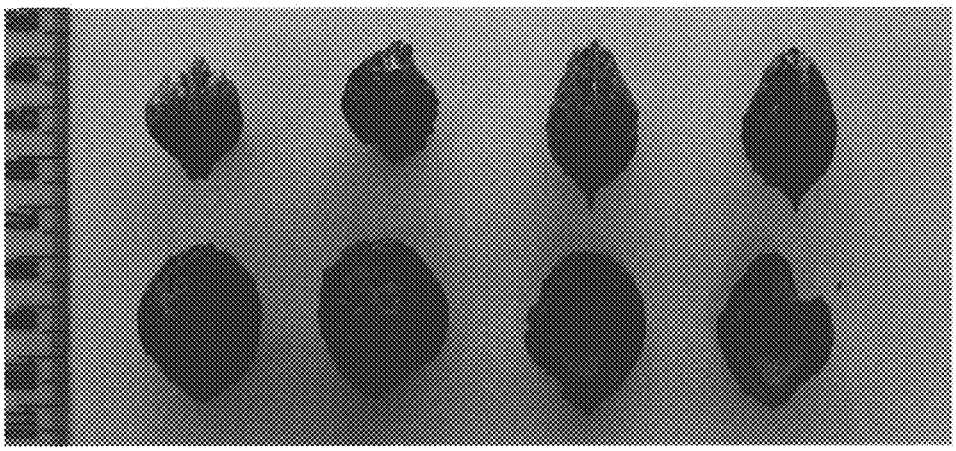
FIG. 3. Color photograph of the endocarp of 'Golden Zest'. The ruler is demarcated in millimeters.
Figure 4:
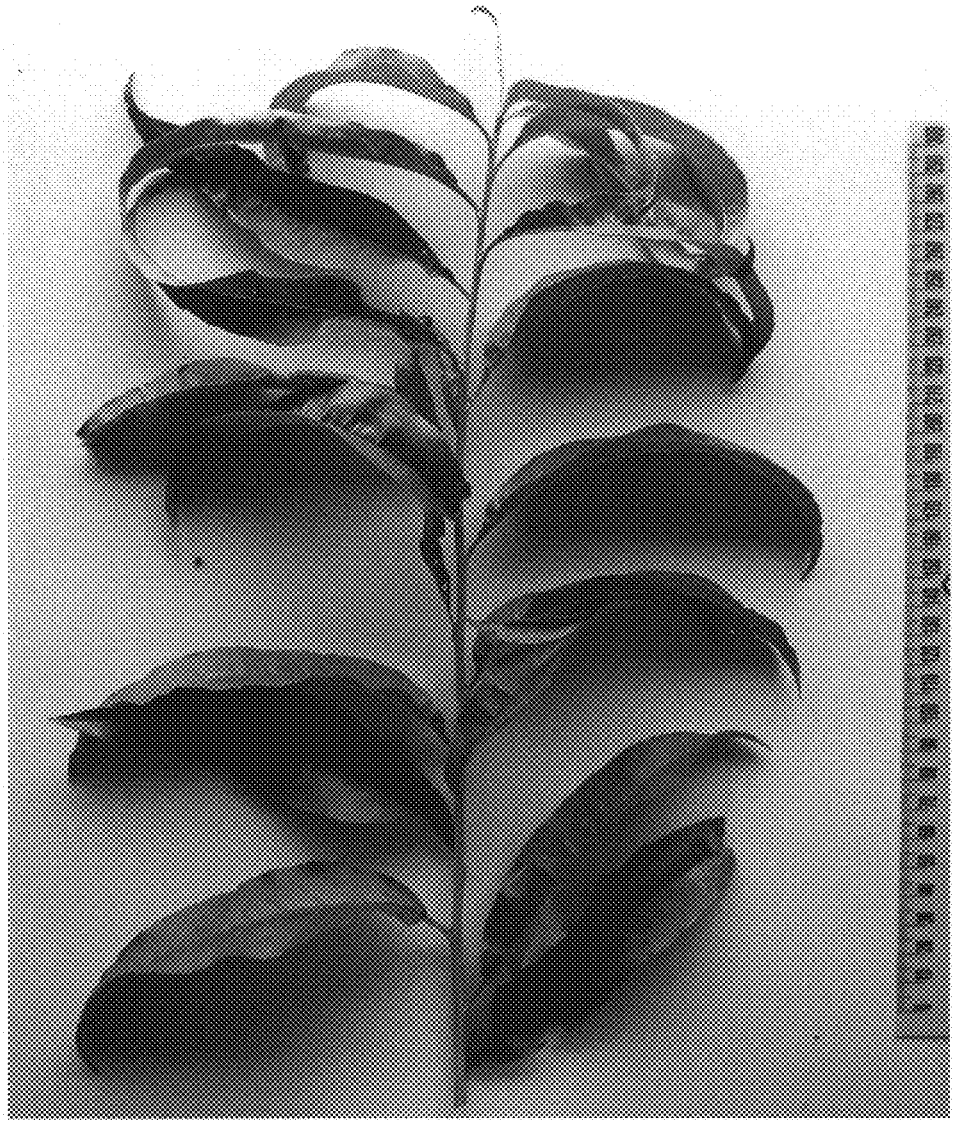
FIG. 4. A shoot showing the leaves of the 'Golden Zest' peach. The ruler is demarcated in millimeters.
Figure 5:
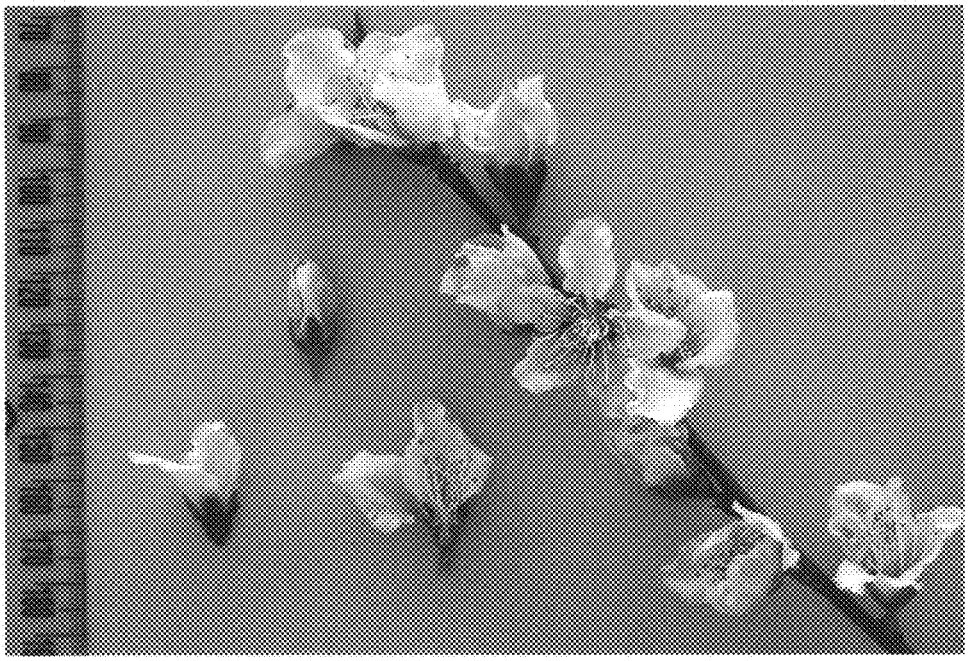
FIG. 5. The showy flowers of 'Golden Zest'. The ruler is in millimeters.

Referring more specifically to the pomological details of this new and distinct variety of peach tree, the following has been observed under the ecological conditions prevailing at the experimental orchards in the medium chill zone of Texas (Fairfield and College Station, Tex). All major color code designations are by reference to The R.H.S. Colour Chart (2001) provided by The Royal Horticultural Society of Great Britain. Colors are approximate as color depends on horticultural practices such as light level and fertilization rate, among others.

Tree:

*Size*.—Generally average to above average as compared to other common peach cultivars ripening in the mid-season of maturity.

*Height*.—7 feet (2.13 m) at the end of the 2012 growing season.

*Width*.—8 feet (2.43 m) at the end of the 2012 growing season.

*Vigor*.—High.

*Density*.—Medium.

*Productivity*.—Productive.

*Shape*.—The trees are vigorous with the typical semi-spreading growth habit similar to 'TexKing' (U.S. Plant Pat. No. 14,627), 'TexPrince' (U.S. Plant Pat. No. 14,629, and 'TexRoyal' (not patented, Byrne and Bacon, 1991).

*Current season growth*.—The current season growth for the new variety was approximately 2.9 to 4.0 feet (0.88-1.2 m).

*Regularity of bearing*.—Regular, and considered hardy under typical climatic conditions found in the medium chill zone of Texas and in the central San Joaquin Valley, Calif.

Trunk:

*Size*.—Approximately 5.5 inches (13.97 cm) in diameter and 21.0 inches (53.34 cm) in circumference when measured at a distance of approximately 12 inches (30.5 cm) above the soil level, at the end of the 2012 growing season on a five-year old tree.

*Bark texture*.—Considered moderately rough with numerous folds of papery scarf-like skin being present.

*Bark coloration*.—Variable, RHS colors present are 166A-D of the Greyed-Orange Group, N200D of the Brown Group and 201D of the Grey Group.

Branches:

*Size*.—Considered medium for the variety.

*Thickness*.—Average (about 7.0 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 3 to 6 mm in width and were approximately 1 mm in height.

*Current season shoots*.—Surface texture — Substantially glabrous.

*Internode length*.—Approximately 1.9 to 2.8 cm as measured in the middle of a current season stem.

*Color of mature branches*.—The predominant RHS colors are 166A and 177A of the Greyed-Orange Group and 201C-D of the Brown Group.

*Current season shoots*.—Color — Light green (144B, N144C-D and 145A-B of the Yellow-Green Group) with some reddish-brown coloration appearing on exposed surface of the shoots (Grey-Brown Group 199A-B and N199C-D). Type of bearing — long shoots only. Spur length — not applicable. Vegetative bud size — generally 3.0-4.0 mm in length on the mid portion of a late summer shoot. Vegetative bud shape of apex — acute. Position of the vegetative bud in relation to one-year-old shoot — slightly held out.

Leaves:

*Size*.—Considered moderately small for the species. Leaf measurements have been taken from vigorous upright current season growth approximately at mid-shoot.

*Leaf length*.—Approximately 130 to 162 mm.

*Leaf width*.—Approximately 30 to 42 mm.

*Leaf thickness*.—Less than 1 mm.

*Leaf form*.—Lanceolate.

*Leaf tip form*.—Acuminate.

*Leaf upper surface color*.—Green (approximately 137A-C of the Green Group).

*Leaf lower surface color*.—Green (146A-B and 147B of the Yellow-Green Group).

*Leaf mid-vein color*.—Light yellow green (N145C and 154C-D of the Yellow Green Group and 160C of the Greyed-Yellow Group).

*Leaf margins*.—

*Form*.—Considered crenate.

*Uniformity*.—Considered generally uniform.

*Leaf petioles*.—Size — Considered medium long. Length — Approximately 8 to 13 mm. Thickness — Approximately 1 to 2 mm. Color — Light yellow green (Yellow-Green Groups N145C and 154C-D and 160C of the Greyed-Yellow Group).

*Leaf glands*.—Size — Approximately 1 mm in height and width. Number — Generally 0-2 per leaf. Type — Globose. Color — Brown with green (199A and N199B-D of the Grey-Brown Group, N145C and 154C-D of the Yellow Green Group and 160C of the Greyed-Yellow Group). Position of leaf glands — predominantly on the base of the leaves.

*Leaf stipules*.—Size — Medium-large for the species. Length — Approximately 12 to 15 mm. Form — Lanceolate. Color — Green (144B-C of the Yellow-Green Group) with reddish brown tips (approximately 165B and 166C-D of the Greyed-Orange Group) when young. The stipules are considered to be early deciduous. Ratio of wood (leaf) buds to flowering buds — 1 to 2 flower buds per vegetative bud.

Flowers:

*Floral buds*.—General — The floral buds are considered to be medium to medium large in size, conic in form, and slightly appressed relative to the bearing shoot. Color — The bud scales are silver-gray, (approximately 197A of the Greyed-Green Group and N200A-B of the Brown Group The buds are considered hardy under the typical climatic conditions of the medium chill zone of Texas and the central San Joaquin Valley, Calif. Length — Approximately 5 to 7 mm. Blooming Type — Considered medium early in relation to other peach cultivars commonly growing in the medium chill zone of Texas. Date of full bloom was between March 1st and March 15$^{th}$ during the period between 2006 and 2011. Mean bloom date was March 6$^{th}$ which is about 5 days before 'June Gold' is in full bloom. Flower fertility — self-fertile. Flower Type — Showy. Flower Size — Flower diameter at full bloom is approximately 32 to 37 mm. Bloom Quantity — Considered abundant. Flower Bud Frequency — Normally 1 to 2 per node.

*Petal size*.—General — Considered medium to medium large for the species. Width — Approximately 13 to 14 mm. Length — Approximately 17 to 20 mm. Petal Form — Broadly ovate. Petal Count — Nearly always 5. Petal Color — Medium pink (Red-Purple Group 62C, 69A, 73D and Purple Group 75D). Flower arrangement of petals — free or slightly overlapping when the flower is completely open.

*Petal claw*.—Form — The claw is considered truncate in shape and has a medium size when compared to other varieties. Length — Approximately 1 to 1.5 mm. Width — Approximately 1 mm. Petal Margins — Generally considered variable, from nearly smooth to slightly undulate. Petal Apex — Generally — The petal apices appear slightly domed.

*Flower Pedicel*.—Length — Considered short with an average length of 2-3 mm. Thickness — Considered average, approximately 1 mm. Color — A light green (Yellow-Green Group 144C-D and N144C-D). Floral Nectaries — Color — Bright orange (Orange Group 24A, 25A-C, N25A-B and 28A-B).

*Calyx*.—Surface Texture — Generally glabrous. Color — Red-purple with green (Yellow-Green Group 144A-B, N144C-D, Greyed-Orange Group 176A, Greyed-Red Group 178A, Greyed-Purple Group 183A-B, 185A, N186C and 187A-B).

*Sepals*.—Surface Texture — The surface has a short, fine, wooly and a gray-colored texture. Size — Average, and ovate in form. Color — Red-purple with green (Yellow-Green Group 144A-B, N144C-D, Greyed-Orange Group 176A, Greyed-Red Group 178A, Greyed-Purple Group 183A-B, 185A, N186C and 187A-B).

*Anthers*.—General — Average in size for the species. Color — Golden yellow with brown (Yellow-Orange Group 17A-B, 21A-B and Brown Group N200A). Position with respect to pistil — generally at the same height or higher. Position with respect to the petals — anthers do not protrude when the flowers are at the pink bud stage Pollen Production — Pollen is abundant, and is a yellow color.

*Filaments*.—Size — Variable in length, approximately 12 to 16 mm, with the filaments longer or equal to the pistil. Color — White (approximately White Group 155A-D) and becoming dark pink (approximately Red-Purple Group 60D) with advanced maturity.

*Pistil*.—General — Average in size, but slightly longer shorter or equal to the anther height. Length — Approximately 16 to 18 mm, including the ovary. Color — Considered light green (Yellow-Green Group 151A). Surface Texture — The variety has a long, silver white pubescent pistil (approximately RHS White Group 155A-D).

Fruit:

*Maturity when described*.—The present variety of fruit is described, as it would be found in its firm ripe condition at full commercial maturity. Under the ecological conditions prevailing in the medium chill zone of Texas 'Golden Zest' ripens in mid to late June, about 3 weeks after 'June Gold'.

*Size*.—General — Medium large to large for the season and considered uniform.

*Average cheek diameter*.—Approximately 71 to 73 mm.

*Average suture diameter*.—Approximately 67 to 72 mm.

*Average axial diameter*.—Approximately 60 to 67 mm.

*Fruit form*.—Generally round. Rarely the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex. Little callusing or stitching exists along the suture line. Fruit suture depth — generally even to up to 2 mm depth. Color — Medium to dark red (Orange-Red Group 33B-C and Red Group 41A). Ventral Surface — Form — Considered uniform.

*Stem cavity*.—Size — Considered large for the species. Length — Approximately 23 to 27 mm. Width — Approximately 12 to 14 mm. Depth — Approximately 12 to 18 mm. Fruit Base — Round. Fruit Apex — Flat.

*Fruit stem*.—i) Length — Approximately 10 mm. ii) Thickness — Approximately 5 mm. iii) Color — Light green (approximately Green Group 142A).

*Fruit skin*.—i) Generally considered medium or average in thickness. ii) Surface Texture — thick pubescence. iii) Skin Acidity — Considered neutral. iv) Tenacious to Flesh — Yes at commercial maturity. v) Tendency to Crack — Not observed. vi) Skin Color — Generally — Variable, with approximately 40-65% of the fruit surface covered with an attractive orange red blush. vii) Down — Long and thick. viii) Blush Color — The blush color is generally more prevailing apically. This blush ranges in color from a medium to a dark red (Red Group 42A-46A) with many degrees of shading and blending occurring between these colorations. ix) Skin Ground Color — Medium yellow (Yellow Group 8A-B).

*Flesh color*.—Medium orange-yellow (Yellow-Orange Groups 16A-B and 17B-C).

*Flesh fibers*.—Present, numerous and lightly colored. These fibers are present throughout the flesh.

*Stone cavity color*.—Dark orange-yellow (Yellow-Orange Group 23A).

*Flesh texture*.—Generally, the flesh is considered very firm and fine at commercial maturity.

*Ripening*.—Generally the fruit of the present variety ripens evenly.

*Flavor*.—Considered sweet with slightly acidic flavor.

*Soluble solids*.—Range from 11 to 13 Brix with a mean of 11.7 Brix as grown in the medium chill zone of Texas.

*Titratable acidity*.—This peach has a medium level of acidity which generally ranges from about 0.6 to 0.83% titratable acidity.

*Aroma*.—Pleasant and reasonably abundant.

*Eating*.—Generally considered very good.

Stone:

*Attachment*.—Clingstone at commercial maturity.

*Stone size*.—i) Generally considered medium to medium-large relative to the ratio of stone to fruit size. ii) Length — Approximately 32 to 36 mm. iii) Width — Approximately 23 to 26 mm. iv) Thickness — Approximately 17 to 19 mm.

*Fibers*.—Generally several medium length fibers are attached along the entire surface of the stone.

*Stone form*.—Elliptical.

*Stone base angle*.—Medium.

*Apex shape*.—Medium.

*Stone shape*.—Considered elongated.

*Stone surface*.—i) Surface Texture — Is honeycombed with single pits, chains of pits and line grooves. ii) Ridges — A few ridges are present basally, and converge towards the base of the stone.

*Ventral edge*.—Small to medium.

*Dorsal edge*.—Shape — Grooved and having moderately rough edges.

*Stone color*.—The color of the dry stone is dark brown (165A of the Greyed-Orange Group, N199B-C of the Grey-Brown Group and 200D of the Brown Group). The color of the inside surface of the endocarp is primarily 165B-D of the Greyed-Orange Group.

*Tendency to split*.—Splitting has not been observed.

*Kernel*.—The kernel fills the endocarp at harvest and measures approximately 5 mm in thickness, 11-12 mm in width, and 16-20 mm in length. The colors of the fresh kernel are primarily a tan color (Yellow Group 8C-D and Greyed-Orange Group 163A-B) When dried the shriveled kernels measure approximately 3-4 mm in thickness, 11-12 mm in width, and 16-19 mm in length. The colors of the shriveled kernels are primarily Greyed-Orange Group 166D. The kernel is viable if stratified without allowing the seed to dry out.

*Use*.—The subject variety, 'GOLDEN ZEST', is considered to be a peach tree of mid-season maturity, which produces non melting yellow-fleshed fruit which are very firm, with an attractive golden-yellow skin coloration, and which are useful for both local and long distance shipping.

*Keeping quality*.—Good to very good.

*Resistance to insects and disease*.—No particular susceptibilities were noted.

*Shipping quality*.—Above average.

Although the new variety of peach tree possesses the described characteristics when grown under the ecological conditions prevailing near Fairfield, Freestone county, Tex. it will be understood that variations of the usual magnitude and characteristics incident to the changes in growing conditions, fertilization, pruning, and pest control are to be expected.

References

Bradford, L. G. and N. G. Bradford, 1972. Nectarine tree. 'Red Diamond'. U.S. Plant Pat. No. 3,1165.

Bradford, L. G. and N. G. Bradford. 1992. Peach tree (Crimson Lady). U.S. Plant Pat. No. 7,953. Aug. 25, 1992.

Brooks, R. M. 1958. Double Delight, Earligold, and June Gold peaches. Fruit Var. J. 3:22.

Okie, W. R., D. W. Ramming, and R. Scorza. 1985. Peach, nectarine, and other stone fruit breeding by the USDA in the last two decades. HortScience 20: 633-641.

Raseira, M. C. B., B. H. Nakasu, A. M. Santos, J. F Fortes, O. M. Martins, A. Raseira, and J. Bernardi. 1992. The CNPFT/EMBRAPA fruit breeding program in Brazil. HortScience 27: 1154-1157.

We claim:

1. A new and distinct *Prunus persica* tree, substantially as illustrated and described herein.

* * * * *